United States Patent [19]

Bauer

[11] Patent Number: 4,904,699

[45] Date of Patent: Feb. 27, 1990

[54] NIFEDIPINE CONCENTRATE STABILIZED AGAINST THE INFLUENCE OF LIGHT AND A PROCESS FOR ITS PREPARATION

[76] Inventor: Kurt H. Bauer, Im Finkeler 4, 7800 Freiburg, Fed. Rep. of Germany

[21] Appl. No.: 129,767

[22] Filed: Dec. 7, 1987

[30] Foreign Application Priority Data

Dec. 18, 1986 [EP] European Pat. Off. ........ 86117660.0

[51] Int. Cl.$^4$ ........................................... A61K 31/395
[52] U.S. Cl. .................... 514/972; 514/277; 514/970
[58] Field of Search ................ 514/937, 359, 404, 972

[56] References Cited

U.S. PATENT DOCUMENTS

| 4,412,986 | 11/1983 | Kawata | 514/788 X |
| 4,446,325 | 5/1984 | Ohno | 546/283 |
| 4,693,892 | 9/1987 | Hegasy | 514/972 X |
| 4,711,902 | 12/1987 | Serno | 514/356 |

Primary Examiner—William R. Dixon, Jr.
Assistant Examiner—James M. Hunter, Jr.

[57] ABSTRACT

A nifedipine concentrate stabilized against the influence of light is described, characterized in that it contains nifedipine, polyethylene glycol, from 0.5 to 20% by weight of Vitamin $B_2$, based on the nifedipine, at least one surface-active agent and optionally conventional carriers. A process for the preparation of the nifedipine concentrate and a medicament containing nifedipine and its use for the production of pharmaceutical preparations are also described.

16 Claims, 2 Drawing Sheets

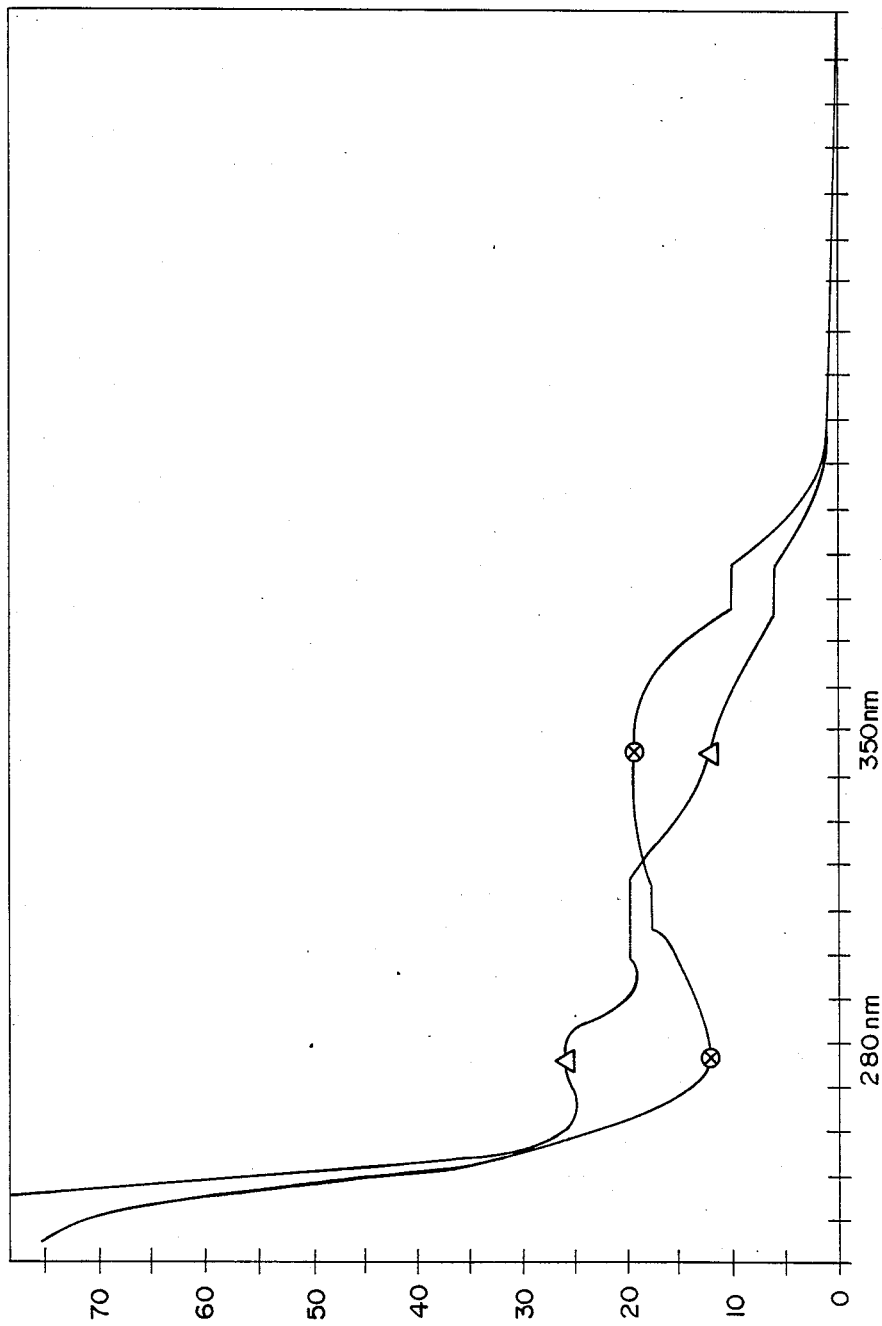

NIFEDIPINE CONCENTRATE STABILIZED AGAINST THE INFLUENCE OF LIGHT AND A PROCESS FOR ITS PREPARATION

This invention relates to a nifedipine concentrate which is stabilized against the influence of light, to a process for its preparation, a medicament containing this compound, and its use.

Nifedipine is a very difficultly soluble calcium antagonist which does not dissociate and is extremely sensitive to light. Nifedipine will dissolve in water only to an extent of about 1:200,000 and is sparingly soluble in ethanol and in glycerol but more readily soluble in chloroform and acetone.

Owing to the sensitivity of nifedipine to light and its low solubility, numerous difficulties arise in the galenic preparation of medicament specialities, as has been documented by numerous Patents and Patent Applications for special formulations of this active substance.

The sensitivity of nifedipine to daylight and UV light can best be expressed by the half life of a nifedipine solution in daylight, which amounts to only a few minutes (K. Thoma et al., PHARM.IND. 47, 207–215, 319–327 (1985)). This sensitivity to light is considerably greater than that of most known pharmaceutical agents. Nifedipine can therefore only be treated and made up into pharmaceutical preparations in complete darkness or at the most in red and yellow light.

Owing to its low solubility, nifedipine has hitherto in most cases been embedded in soluble, hydrophilic polymers such as polyethylene glycols, polyvinyl pyrrolidone or cellulose ethers. This gives rise to solid solutions if it dissolves in the molten form of, for example, polyethylene glycol, or to coprecipitates, for example when nifedipine is dissolved in polyvinyl pyrrolidone with suitable solvents and then precipitated in a very finely divided form by removal of the solvents.

The known solid solutions in polyethylene glycol contain at least three times the quantity of polyethylene glycol. Surface-active agents or similar compounds may be added to these solid solutions or to the coprecipitates if necessary.

In DE-OS 3 438 830, which corresponds to EP-A-0 182 007, there is described a form of preparation containing nifedipine as active ingredient in which the nifedipine, which is present as molecular dispersion in the form of a solidified melt in a mixture of liquid and non-liquid polyethylene glycols, is filled into hard gelatine capsules in the form of this melt. The dye "Yellow Orange S" is used to improve the stability. The advisability of using Yellow Orange S as dye is doubtful since it is an azo dye.

The extraordinarily high sensitivity of nifedipine to light is allowed for by operating in the dark or in red or yellow light. Furthermore, preparations containing the medicament, nifedipine, are filled into soft gelatine capsules, as described, for example, in LU-A 65 929, or wrapped in films which have been coloured with Yellow Orange S, food yellow No.4 or 5 or iron oxide colours (e.g. E 110) and titanium dioxide to filter out the light. The incorporation of UV absorbents, such as phenyl salicylate, is also customary. Packaging materials may be coloured with suitable dyes. In such an arrangement, the active ingredient and the dye are strictly separated from one another.

The testing of suntan creams is described in C.A. 66, No.23 (1967), Ref. 108175n, with the results showing an activity approximately corresponding to that which would be expected in vivo on the skin. One example is a mixture of red veterinary petrolatum and riboflavin. It is not clear from the report whether red veterinary petrolatum protects against light on its own or whether the light protective action is only obtained after the addition of riboflavin which, however, is insoluble in vaseline and in the case described is not incorporated in a dissolved form.

The high sensitivity to light and low solubility of nifedipine require elaborate methods of procedure for the production of the pharmaceutical preparations.

It is an object of the present invention to overcome the disadvantage of the previously known preparations containing nifedipine and to provide a nifedipine concentrate from which it is possible, without large quantities of additives, to make up pharmaceutical preparations from which the nifedipine can be rapidly released in sufficiently high concentrations. The nifedipine concentrate according to the invention should also have a higher resistance to light than nifedipine itself. It is an object of the invention to provide a process for the production of pharmaceutical preparations containing nifedipine by which the relatively poorly soluble nifedipine can be incorporated in a sufficiently finely dispersed form in matrices (for embedding) so that the release of the medicament and the speed with which it dissolves are improved. According to this invention, incorporation of the extremely difficultly soluble nifedipine in a very finely dispersed form, either dissolved as a molecular dispersion or suspended or dispersed (undissolved) should be achieved in very small agglomerated molecular groups in order to ensure rapid and sufficient release (speed of solution) and ultimately optimum resorption.

According to the invention, improvement in the protection against light should be achieved by as far as possible harmless additives, for example by the addition of a vitamin.

The present invention relates to a nifedipine concentrate which is stabilized against the action of light, characterised in that it contains nifedipine, polyethylene glycol, from 0.5 to 20% by weight of Vitamin $B_2$, based on the nifedipine, at least one surface active agent and optionally the usual carrier materials.

The surface-active agents selected and incorporated according to the invention enable nifedipine to be dissolved even at higher concentrations. The residue which is not dissolved is so finely dispersed by the surface-active agents that it behaves virtually like dissolved nifedipine.

When Vitamin $B_2$ is used with nifedipine, the problem arises that these two substances differ in their solubility and their stability. In the past, either dyes or different active ingredients or UV absorbents have been used. It has now surprisingly been found that Vitamin $B_2$ has a good light protective action for nifedipine. The physical incompatibility which is due to the different solubilities of nifedipine and Vitamin $B_2$ could surprisingly be overcome by the balanced combination of PEG, organic solvents, a suitable surface-active agent and the required quantity of water.

In the past, solid solutions or precipitates of nifedipine were prepared in ratios of at least 1:3. The mixture of polyethylene glycol and the given surface active agents enable higher concentrations of nifedipine to be obtained with a comparable speed of solution or bio availability.

This invention relates to a process for the preparation of nifedipine concentrates which are stabilized against the influence of light, characterised in that nifedipine, polyethylene glycol and optionally the surface active agent are dissolved in an organic solvent, optionally with heating, and an aqueous solution or suspension of Vitamin $B_2$ and optionally surface-active agent is added to the solution containing nifedipine, at least one of the two solutions or the suspension containing surface active agent, and the two solutions are mixed and concentrated by evaporation in known manner and the stabilized product of embedding is isolated and optionally granulated.

The difficulty in producing the pharmaceutical preparation according to the invention is that nifedipine is only soluble in certain organic solvents while Vitamin $B_2$ is only soluble in water. It is therefore necessary first to dissolve the Vitamin $B_2$ in water as far as possible and then to suspend the insoluble remainder. It is not possible to use too much water because the nifedipine precipitate would be suspended when the components are mixed and because the drying times would be too long. It has surprisingly been found that the aqueous solution or suspension can be sufficiently finely dispersed due to the presence of polyethylene glycol and the surface-active agent.

This invention also relates to a pharmaceutical preparation containing nifedipine, polyethylene glycol, from 0.5 to 20% by weight of Vitamin $B_2$, based on nifedipine, at least one surface-active agent and conventional pharmaceutical carriers and optionally diluents.

The invention also relates to the use of the nifedipine concentrate mentioned above for the production of pharmaceutical preparations.

It has surprisingly been found that with the aid of suitable solvents, nifedipine can be embedded in polyethylene glycol at ratios of only 1:1. It was also surprising to find that an unexpectedly high protection against light is obtained by the incorporation of Vitamin $B_2$ into nifedipine.

According to this invention, nifedipine can be dissolved or embedded in polyethylene glycol in ratios of only 1:1 by the aid of suitable solvents such as acetone, chlorinated hydrocarbons or toluene which are subsequently removed. The ratio of nifedipine to polyethylene glycol may lie in the range of from 2:1 to 1:3.

Nifedipine has its highest solubility, namely about 30%, in acetone and various hydrocarbons, in particular certain chlorinated hydrocarbons. Other solubilities are as follows:

| | |
|---|---|
| in alcohols (ethanol) | about 2.6% |
| in Tween | about 2% |
| in Solketal | about 3% |
| in 1,2-propylene glycol | about 64% |
| in benzoyl alcohol | about 11% |
| in PEG 400 | 6.1% |
| in castor oil | 0.54% |
| in liquid paraffin | <0.05%. |

Surprisingly high protection against light is obtained by the incorporation of from 0.5 to 20% by weight, preferably from 5 to 10% by weight of Vitamin $B_2$ (riboflavin, lactoflavin), based on the quantity of nifedipine. The Vitamin $B_2$ must be incorporated to a large extent in a dissolved form. From 5 to 20 parts of water per 1 part of Vitamin $B_2$ are generally required for this.

To optimize the combination or emulsification of Vitamin $B_2$, which is hydrophilic, with nifedipine, which is hydrophobic, it is necessary to add at least one suitable surface active agent. Substances suitable for this purpose are ethoxy-propoxy copolymers (e.g. Pluronics ®), polyoxyethylene fatty acid esters and polyoxyethylene fatty alcohol ethers, ethoxylated, hydrogenated castor oil products (e.g. Cremophor RH 60 ®) and similar compounds. Mixtures of surface-active agents may also be used. The surface-active agent is incorporated in a quantity of from 2 to 50 parts, preferably from 5 to 25 parts, based on 50 parts of nifedipine.

The addition of surface-active agents not only facilitates dispersion between the hydrophobic nifedipine and hydrophilic Vitamin $B_2$ but also improves the release or bio availability of nifedipine.

This is the reason why the concentration of nifedipine could be increased in the preparations according to the invention.

For the preparation of the nifedipine concentrates according to the invention, nifedipine and polyethylene glycol are dissolved in the solvent, optionally with heating, and a solution or suspension of Vitamin $B_2$ in water is added.

The solution or dispersion obtained is then dried. Drying may be carried out in known manner, for example by spray drying or by solidification on cooling rollers. If the product is left to cool on rollers, it is size reduced after drying, for example by grinding or granulating.

The nifedipine concentrates according to the invention may be worked up in known manner by mixing them with the usual pharmaceutical carriers or melting them together with the usual auxiliary agents to form pulverulent mixtures or granulates which may be used as medicaments in known manner. The granulates, for example, may be filled into hard gelatine capsules or compressed to form tablets. Soft gelatine capsules and drops may also be prepared by dissolving the concentrate in liquid polyethylene glycols, other glycols or glycerol with menthol and similar auxiliary substances.

The improvement in stability to light is illustrated by the accompanying UV spectral photometric graphs. According to S. Ebel et al., ARZNEIM.FORSCH. 28 (12), 2188–2193 (1978) and K. Thoma et al., PHARM.IND. 47 (2), 207–215 (1985), the UV spectrum of nifedipine changes during exposure to light, e.g. daylight, in that a peak forms at 280 nm and the plateau at about 350 nm falls. When the shifts in the accompanying UV graphs are compared with the initial graphs the shifts in the case of embedded nifedipine which has been stabilized with riboflavin, show that an improvement in stability to light by about two thirds is obtained after three days exposure to light, i.e. the instability is now only about one third of that of the product which has not been stabilized.

FIG. 2 represents embedding of nifedipine without riboflavin.

Figure 1:
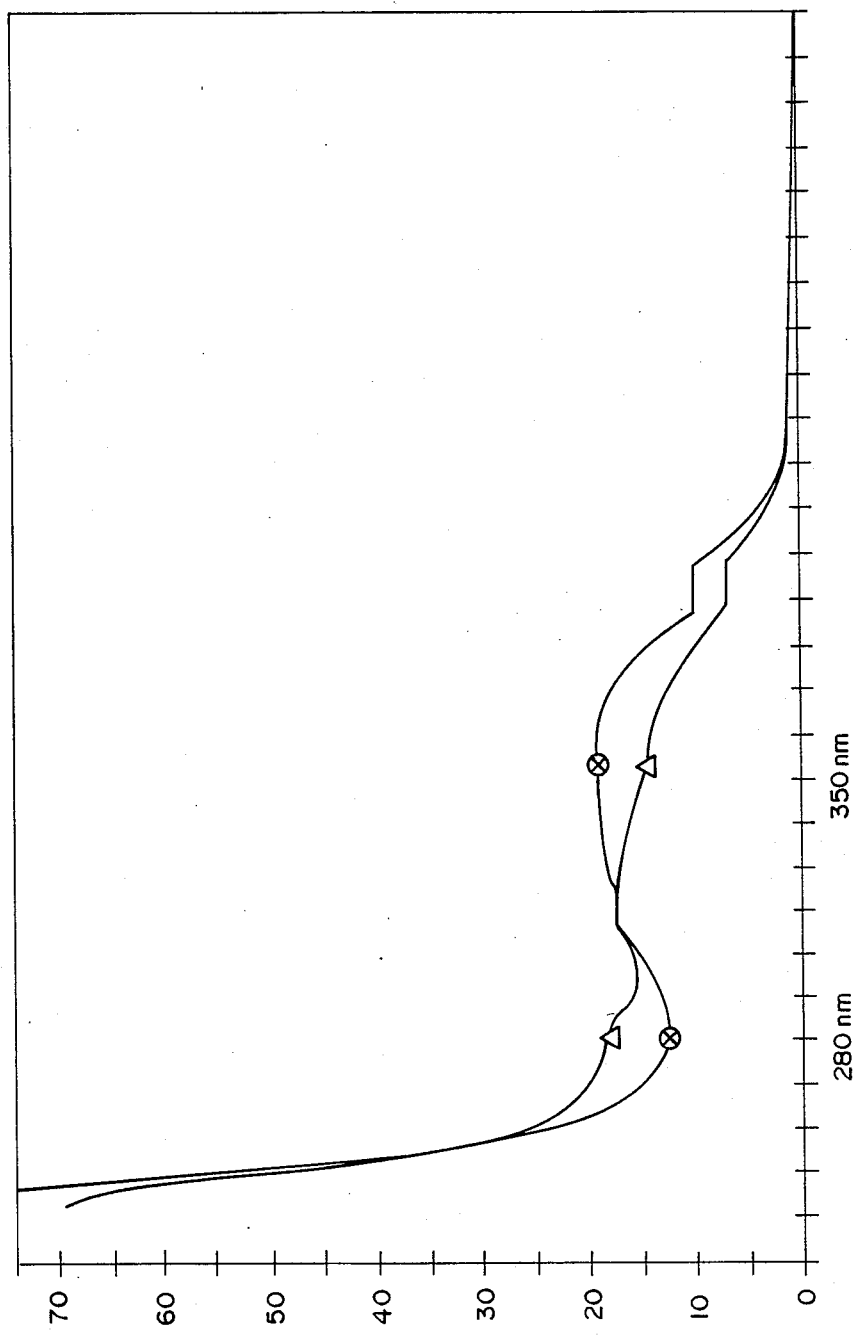
FIG. 1 represents embedding of nifedipine with riboflavin.

In each of FIGS. 1 and 2, the graph through the circles containing an x represents the initial graph and the graph through the filled in triangles represents the shift after 3 days exposure to light.

The advantage obtained is that owing to the addition of Vitamin $B_2$ in an extremely finely dispersed form it is no longer necessary to protect absolutely against light during the stages of preparation and the resistance of the end products to light is also improved.

The following Examples illustrate the invention.

EXAMPLE 1

50 Parts of nifedipine are dissolved in a heated solution (about 60° to 80° C.) of 10 parts of Poloxamer 188 ® and 35 parts of polyethylene glycol 6000 in 60 to 80 parts of toluene.

5 Parts of riboflavin phosphate sodium are dissolved separately in 40 parts of water and in part suspended. The two solutions are then combined and thoroughly mixed. The stabilized embedding product is prepared by spray drying in known manner. The reaction mixture obtained may also be solidified on cooling rollers after evaporation of the solvent. In that case, the resulting product is granulated before further use.

EXAMPLE 2

50 Parts of nifedipine are dissolved in 50 parts of chloroform with mild heating. 43 Parts of molten polyethylene glycol 10,000 are added. Separately thereto, 2 parts of riboflavin, soluble in a warm solution of 5 parts of Cremophor RH 60 ® and 15 parts of water, are homogeneously dispersed therein. The two preparations are then combined and then worked up into an embedding product as described in Example 1.

EXAMPLE 3

50 Parts of niphedipine are dissolved in a mildly heated solution of 30 parts of Tagat RH 40 ® and 49 parts of polyethylene glycol 20,000 in 75 to 90 parts of acetone. Separately thereto, 1 part of riboflavin soluble in 5 parts of water is partly dissolved and partly suspended. The two preparations are combined and the stabilized embedding product is prepared as described in Example 1.

EXAMPLE 4

50 Parts of nifedipine are dissolved in 100 parts of cyclohexanol with mild heating and 27 parts of molten polyethylene glycol 4000 are added. Separately thereto, 3 parts of riboflavin phosphate sodium are substantially dissolved in a warm solution of 20 parts of polyethoxy-50-stearate and 30 parts of water. The two preparations are combined and then worked up to form an embedding product as described in Example 1.

EXAMPLE 5

Soft gelatine capsules are prepared by dissolving, per capsule, 20 mg of the embedded nifedipine prepared according to Examples 1 to 4 in 358.9 mg of polyethylene glycol 300 or 400, and 0.6 mg of peppermint oil and a solution of 0.5 mg of saccharine sodium in 5 mg of water are then added.

This solution is introduced into soft gelatine capsules in known manner so that each capsule contains 10 mg of pure nifedipine.

EXAMPLE 6

For the preparation of film tablets, the embedded nifedipine prepared according to Examples 1 to 4 is homogeneously mixed, in a quantity of 40 mg per tablet, with 50 mg of Tablettose*, 40 mg of microcrystalline cellulose, 19 mg of corn starch or wheat starch and 1 mg of magnesium stearate and passed through a sieve with a clear mesh width of 0.1 to 0.15 mm.

This mixture is compressed in known manner to form tablets having a gross weight of 150 mg and containing 20 mg of pure nifedipine. Each tablet is subsequently coated with a film which is coloured with iron oxide pigments for protection against light.

EXAMPLE 7

For the preparation of a mixture for hard gelatine capsules, the embedded nifedipine according to the invention prepared according to one of the Examples 1 to 4 is mixed in a quantity of 20 mg per capsule with 30 mg of microcrystalline cellulose, 25 mg of dicalcium phosphate, 20 mg of starch and 5 mg of talc and the mixture is sieved. This mixture is filled into hard gelatine jointed capsules in known manner to contain the prescribed amount of active ingredient.

I claim:

1. Nifedipine concentrate stabilized against the influence of light, comprising nifedipine, polyethylene glycol, from 0.5 to 20% by weight of Vitamin $B_2$, based on the nifedipine, and at least one surface-active agent.

2. Nifedipine concentrate according to claim 1, wherein the ratio of nifedipine to polyethylene glycol is in the range of from 2:1 to 1:3.

3. Nifedipine concentrate according to claim 1 or 2, containing from 2 to 50 parts of surface-active agent, based on 50 parts of nifedipine.

4. Nifedipine concentrate according to claim 1 or 2, wherein said at least one surface-active agent is selected from the group consisting of ethoxy-propoxy copolymers, polyoxyethylene fatty acid esters, polyethylene fatty alcohol ethers, ethoxylated, hydrogenated castor oil products and mixtures of these compounds.

5. Nifedipine concentrate according to claim 1 containing additionally a conventional carrier.

6. A process for the preparation of a nifedipine concentrate stabilized against the influence of light, comprising:
   (a) dissolving nifedipine and polyethylene glycol in an organic solvent to form a solution,
   (b) adding to the solution of (a) an aqueous solution or suspension of Vitamin $B_2$, at least one of the solution of (a) or said aqueous solution or suspension of Vitamin $B_2$ also containing surface-active agent,
   (c) mixing the result of (b),
   (d) concentrating by evaporation the result of (c) to isolate a stabilized product.

7. Process according to claim 6 wherein the organic solvent used is selected from the group consisting of acetone, chlorinated hydrocarbons and toluene.

8. Process according to claim 6 or 7, wherein nifedipine and the polyethylene glycol are used in a ratio of from 2:1 to 1:1 and wherein from 0.5% to 20% by weight of Vitamin $B_2$ is used, based on the quantity of nifedipine.

9. Process according to one of the claims 6 or 7 wherein the surface-active agent is used in a quantity from 2 to 50 parts, based on the nifedipine.

10. Process according to claim 6 wherein the dissolving in (a) is accomplished with heating.

11. Process according to claim 6 additionally comprising (e) granulating the product of (d).

12. Medicament comprising nifedipine, polyethylene glycol, from 0.5 to 20% by weight of Vitamin $B_2$, based on the nifedipine, at least one surface-active agent and pharmaceutical carriers.

13. Medicament according to claim 12 wherein the ratio of nifedipine to polyethylene glycol is in the range of from 2:1 to 1:3.

14. Medicament according to one of the claims 12 or 13, containing from 2 to 50 parts of surface-active agent, based on 50 parts of nifedipine.

15. Medicament according to claims 12 or 13 wherein the at least one surface-active agent is selected from the group consisting of ethoxy-propoxy copolymers, polyoxyethylene fatty acid esters, polyoxyethylene fatty alcohol ethers, ethoxylated, hydrogenated castor oil products and mixtures of these compounds.

16. Medicament according to claim 12 additionally comprising a diluent.

* * * * *